United States Patent
Laruelle et al.

(12)

(10) Patent No.: US 6,669,957 B1
(45) Date of Patent: Dec. 30, 2003

(54) GALENIC FORMULATIONS FAST DISINTEGRATING IN THE MOUTH AND METHOD FOR PREPARING SAME

(75) Inventors: Claude Laruelle, Villeneuve-Loubet (FR); Noël Zakarian, Marseilles (FR); René Gimet, Valbonne (FR); Dominique Toselli, Nice (FR)

(73) Assignee: CLL Pharma, Nice (FR)

( * ) Notice: Subject to any disclaimer, the term of this patent is extended or adjusted under 35 U.S.C. 154(b) by 0 days.

(21) Appl. No.: 09/831,711

(22) PCT Filed: Sep. 15, 2000

(86) PCT No.: PCT/FR00/02563

§ 371 (c)(1),
(2), (4) Date: Sep. 5, 2001

(87) PCT Pub. No.: WO01/19336

PCT Pub. Date: Mar. 22, 2001

(30) Foreign Application Priority Data

Sep. 15, 1999 (FR) .............................. 99 11513

(51) Int. Cl.⁷ .................................. A61K 9/20
(52) U.S. Cl. ................. 424/465; 424/495; 424/482; 424/484; 424/473; 424/464; 424/467
(58) Field of Search .................. 424/495, 405, 424/482, 484, 473, 464, 467, 465

(56) References Cited

U.S. PATENT DOCUMENTS 5,695,784 A * 12/1997 Pollinger .................... 424/495

6,350,469 B1 * 2/2002 Daggy et al. ................ 424/464

FOREIGN PATENT DOCUMENTS

| EP | 0 376 891 | 12/1989 |
| WO | 97/28788 | 8/1997 |
| WO | WO 99/09958 | * 3/1999 |
| WO | 99/47126 | 9/1999 |

* cited by examiner

Primary Examiner—Thurman K. Page
Assistant Examiner—Konata M. George
(74) Attorney, Agent, or Firm—Lowe Hauptman Gilman & Berner LLP

(57) ABSTRACT

The invention relates to pharmaceutical dosage forms with rapid disintegration in the mouth and to their process of preparation.

These pharmaceutical dosage forms comprise at least one active principle dispersed in a mixture of excipients and are characterized in that the mixture of excipients comprises at least one weakly compressible diluting agent other than trehalose and a copolymer of 1-vinylpyrrolidin-2-one and of vinyl acetate.

Applications: oral administration of a great many active principles (analgesics, antispasmodics, agents used in gastroenterology, agents for combating motion sickness, antimigraines, β-blockers, antihistaminics, antibiotics or antibacterials, antivertigos, hypnotics, and the like).

21 Claims, No Drawings

GALENIC FORMULATIONS FAST DISINTEGRATING IN THE MOUTH AND METHOD FOR PREPARING SAME

The present invention relates to pharmaceutical dosage forms with rapid disintegration in the mouth and to their process of preparation.

In therapeutics, the simplicity of the oral administration of a medicinally active principle has always been regarded as a major advantage, as testified by the great diversity of pharmaceutical dosage forms intended for this administration route (uncoated, coated and effervescent tablets, gelatin capsules, soft capsules, solutions to be dissolved, ready-for-use oral suspensions, and the like).

As regards solid forms, these nonetheless exhibit two disadvantages. First, they require that a liquid capable of facilitating the swallowing thereof be taken in combination. In point of fact, there are numerous situations in which it may be appreciable to be able to take a medicament by the oral route, the ingestion of which does not require the simultaneous absorption of a liquid. Secondly, some patients and in particular children and elderly people experience difficulties in swallowing such that it is difficult and consequently unpleasant for them to ingest a solid pharmaceutical dosage form, even in the presence of a liquid.

As regards liquid forms, they are generally provided in bulky or easily damaged packagings (bottles, glass ampules), which makes them ill suited to outpatient use.

For this reason, numerous studies have been carried out with the aim of developing pharmaceutical dosage forms intended for per os administration which, while being provided in a solid form, are capable, when they are placed in the buccal cavity, of rapidly disintegrating on contact with the saliva to form a suspension which is easy to swallow.

Thus it is that Laboratoires Prographarm have provided, in French Patent Application No. 91 09245, multiparticulate tablets in which the active principle is present in the form of microcrystals coated in ethylcellulose or microgranules and is dispersed in an excipient composed of at least two disintegrating agents of the sodium carboxymethylcellulose or crosslinked polyvinylpyrrolidone type, of one or more swelling agents of the starch, modified starch or microcrystalline cellulose type, and of a direct tableting sugar.

Subsequently, Laboratoires Prographarm, wishing to improve the texture of these tablets as they generate a sandy and pasty feeling in the mouth, developed a technology known under the Flashtab® trade mark which is disclosed in French Patent Application No. 97 09233 and which consists in coating microcrystals of active principle in a polymethacrylate or a cellulose polymer intended to mask the taste thereof and in using, as excipient, a mixture of a disintegrating agent (sodium carboxymethylcellulose, crosslinked polyvinylpyrrolidone) and of a polyol with a short carbonaceous chain, such as mannitol, xylitol or sorbitol, this polyol fulfilling the role of diluting agent with binding properties.

French Patent Application No. 88 15183, on behalf of D. Vacher, discloses tablets intended to facilitate the oral administration of a medicinally active principle mainly, but not exclusively, to children and more particularly to infants and in which the active principle represents at least 60% by weight of the tablets, so as to reduce their size as much as possible, and is dispersed in an excipient composed of a crosslinked cellulose gum and of a swelling agent of the microcrystalline cellulose type or of the starch type.

Having noted that the use of such tablets cannot in practice be envisaged in adults in so far as they can only comprise small doses of active principle, which would imply having to be taken very frequently, D. Vacher has provided, in International Application No. 96/02237, an improvement to these tablets by coating the active principle in a water-dispersible binding agent of the alkylcellulose type to facilitate the wettability of this active principle on contact with the saliva and by dispersing the active principle thus coated in an excipient composed of crosslinked carboxylmethylcellulose, which in this case acts as agent for bursting the tablets, of microcrystalline cellulose, which acts as diluent, and of a water-soluble polyol of the mannitol, xylitol or sorbitol type, which is itself intended to mask the taste of the active principle.

At the same time, some research has been devoted to developing pharmaceutical dosage forms capable of disintegrating in the mouth by a controlled effervescence process.

Thus, for example, International Application No. 91/04757, on behalf of Cima Labs, discloses tablets in which the active principle is dispersed, optionally in a microencapsulated form, in a mixture comprising both an acid of the citric acid, tartaric acid, maleic acid or fumaric acid type and a carbonate, such as sodium bicarbonate, so that this acid and this carbonate react together on contact with the saliva to release carbon dioxide gas and thus to make possible the disintegration of said tablets.

Similarly, French Patent Applications Nos. 94 01457 and 95 03711, on behalf of X. Hesnard, relate to tablets, disintegration of which in the mouth is also obtained by reaction between an acid and a carbonate, the acid in this case being in an amount significantly greater than that of the carbonate, so as to bring about, from the introduction of the tablets into the buccal cavity, a hypersalivation capable of increasing the intrabuccal volume of water, which has the effect of promoting the disintegration of said tablets into a dispersion which can then be imbibed by simple salivary swallowing.

Furthermore, it turns out that the development of a pharmaceutical dosage form capable of rapidly disintegrating in the mouth presents a number of specific problems, in particular because it has to satisfy conditions, some of which conflict with one another. Thus, it has to exhibit a sufficient cohesion and a sufficient hardness not to be detrimentally affected during the various stages of manufacturing, of packaging and of storage, while being capable of disintegrating virtually instantaneously on contact with the saliva. Furthermore, it has to have and to leave in the mouth a pleasant taste, even when the medicinally active principle included therein itself exhibits a pronounced bitterness. Furthermore, it is desirable, although not corresponding to the same requirements as the conventional pharmaceutical dosage forms, for it to be able, however, to be manufactured according to the processes and by means of the same equipment as those used for the manufacture of the latter, so as to render its production cost as satisfactory as possible.

Partial solutions to these problems have been provided in European Patent Applications Nos. 0 553 777, 0 636 364 and 0 745 382.

Thus, European Patent Application No. 0 553 777, on behalf of Takeda Chemicals Industries, discloses a process which consists in mixing the active principle with an excipient mainly comprising one or more carbohydrates of the sucrose, glucose, maltitol, xylitol and erythritol type, in then wetting the resulting mixture with a small amount of water (preferably of between 0.7 and 3%, w/w) and in subjecting it to granulation, and finally, after drying the granules, in tableting the latter. According to this Application, this process would exhibit the two-fold advantage of resulting in the production of tablets possessing a satisfactory hardness and of being able to be put into operation using granulators and tableting machines generally used in the pharmaceutical industry.

European Patent Application No. 0 636 364, on behalf of McNeill-PPC, provides tablets in which an active principle is provided in the form of particles coated with a mixture of cellulose polymers intended to mask the taste thereof and is dispersed in this form in a mixture comprising a compressible carbohydrate capable of disintegrating on contact with water (mannitol, sorbitol, dextrose, sucrose, and the like) and a binder such as cellulose and its derivatives, polyvinylpyrrolidone, starch or microcrystalline cellulose, the purpose of the latter being to confer satisfactory cohesion on the tablets. According to this Application, the coating of the active principle and then the tableting of the coated particles of active principle/compressible carbohydrate/binder mixture can also be carried out by means of equipment with which the pharmaceutical industry is conventionally equipped.

European Patent Application No. 0 745 382, on behalf of Yamanouchi Pharmaceutical, discloses, for its part, tablets exhibiting a hardness capable of preventing them from being broken during manufacturing, packaging and storage operations, which tablets are obtained by a process which consists in subjecting to a granulation, separately or after having mixed them, an active principle, a saccharide of high malleability of the maltose, maltitol or sorbitol type and a saccharide of low malleability, such as lactose, mannitol or glucose, and in then tableting the resulting granules. Here again, this process is presented as being capable of being put into operation using conventional granulators and tableting machines.

Despite all these attempts, it turns out that no solid pharmaceutical dosage form with rapid disintegration in the mouth is entirely satisfactory to date.

This is because the tablets using the Flashtab® technology disclosed in French Patent Application No. 97 09233 provide a sandy and pasty feeling in the mouth, even if this feeling is theoretically less pronounced than that observed with tablets in accordance with French Patent Application No. 91 09245.

It is the same for the effervescent tablets provided in French Patent Application Nos. 91 04757, 94 01457 and 95 03711, these tablets additionally exhibiting a marked astringency because of the high amount of acid included therein.

The coating of the active principle with polymers intended to mask the taste thereof, as disclosed in French Patent Application No. 97 09233 and European Patent Application No. 0 636 364, does not prove to be very effective, so that it does not manage to prevent the development of a bitterness in the mouth, when the active principle itself is bitter. Moreover, this coating significantly complicates the process for the preparation of the tablets.

Finally, many of the tablets disclosed in the abovementioned Patent Applications (FR-A-97 09233, WO-A-96/02237, EP-A-0 636 364, EP-A-0 745 382) are intended to include large amounts of a polyol, such as mannitol, xylitol and sorbitol, the well known laxative effects of which preclude the repeated administration of tablets of this type and, consequently, their use in long-term treatments.

Provision has also been made, in International Application Nos. 97/28788 and 97/28789, for preparing tablets capable of rapidly dissolving in an aqueous medium, but the dissolution of which is not, however, particularly intended to take place in the mouth, from mixtures comprising, in addition to an active principle, trehalose as diluting agent, a binding agent in an amount sufficient to confer a satisfactory hardness on the tablets, which binding agent can in particular be copovidone, and a volatile salt of the ammonium acetate or bicarbonate type, which is removed after the tableting operations and the function of which is to confer, on the tablets, a porosity which is favorable to their dissolution on contact with an aqueous medium.

While envisaging the possibility that the trehalose present in the mixture may just as easily be in the amorphous or crystalline dihydrate form as in the anhydrous form, these Applications teach that, in fact, only the anhydrous trehalose is able, because of its capacity to absorb moisture, to guarantee stability of the active principle and allows the joint use of a volatile salt. In point of fact, it turns out that anhydrous trehalose is not available commercially, so that the preparation of tablets as provided in WO-A-97/28788 and WO-A-97/28789 requires the preliminary preparation of this compound with all the disadvantages which this implies, such as the need to have available specific equipment and the increase in the cost of manufacture of the tablets. The use of a volatile salt itself also significantly complicates the process for the manufacture of the tablets and places a serious burden on the cost, since this salt has to be removed on conclusion of the tableting operations by placing the tablets under vacuum and at a temperature of 60° C. for several hours.

Finally, baclofen-based tablets, which are designed to adhere to one of the buccal mucous membranes and in particular to the palatine mucous membrane, in order to provide for both immediate and sustained release of the baclofen, are known from European Patent Application No. 0 376 891. These tablets are composed of a hydrophilic core, in which the baclofen, a vinyl polymer, a galactomannan (guar gum), a wax or a glyceride are found, and of a thin hydrophobic film which covers the hydrophilic core except for a small surface area, which is that intended to adhere to the mucous membrane. As is illustrated by the examples in this Application, the tablets dissolve in the mouth in 12 to 15 hours. They therefore could not be regarded as tablets with rapid disintegration.

The Applicant Company therefore set itself the target of providing a solid pharmaceutical dosage form which, while being capable of rapidly and completely disintegrating in the mouth so as to limit as far as possible the effort of swallowing needed to ingest an active principle, has a pleasant texture and an acceptable taste, including in the case where the active principle exhibits a pronounced bitterness, exhibits a cohesion and a hardness which are sufficiently high to prevent it from being detrimentally affected during the stages of manufacturing, of packaging and of storage, and can be manufactured by a very simple process, so as to limit the production cost thereof.

This aim is achieved according to the present invention by a pharmaceutical dosage form of the type comprising at least one active principle dispersed in a mixture of excipients and which is characterized in that the mixture of excipients comprises at least one weakly compressible diluting agent other than trehalose and a copolymer of 1-vinylpyrrolidin-2-one and of vinyl acetate. This is because the Applicant Company has found that, by dispersing an active principle in a mixture comprising both a weakly compressible diluting agent, the use of which is, for this reason, recommended in the preparation of pharmaceutical dosage forms requiring granulation by the wet route, and a copolymer of 1-vinylpyrrolidin-2-one and of vinyl acetate, it is possible to obtain, by a simple tableting operation, a pharmaceutical dosage form which, surprisingly, is not only capable of completely disintegrating in an extremely short time, of the order of 30 to 50 seconds, in the buccal cavity but furthermore exhibits:

very pleasant melting in the mouth, an entirely suitable taste, even in the case of pronounced bitterness of the active principle, and satisfactory cohesion and satisfactory hardness, despite the weak compressibility of the diluting agent present in this pharmaceutical dosage form.

Within the meaning of the present invention, the term "weakly compressible diluting agent" is understood to mean any substance capable of being used in pharmaceutical formulating for acting as filler with the aim of obtaining a tablet with suitable characteristics and of a suitable size which exhibits a hardness of between 40 and 50 N when a force of 25 kg/cm$^2$ is applied to a tablet composed of 500 mg of this substance measuring 20 mm in diameter and 4.5 mm in thickness.

According to a first advantageous arrangement of the invention, the weakly compressible diluting agent is chosen from monosaccharides, such as D-glucose monohydrate, anhydrous D-glucose or fructose, disaccharides, such as sucrose, with the exception, however, of trehalose, and dextrates, such as Emdex® from Mendell.

The weakly compressible diluting agent is preferably D-glucose monohydrate, which exhibits the two-fold advantage of being attractive from an economical view point and of being non-cariogenic. This compound is available, for example, from Roquette under the trade name Roferose®.

According to another advantageous arrangement of the invention, the copolymer of 1-vinylpyrrolidin-2-one and of vinyl acetate is copovidone. The latter, which is conventionally used in pharmaceutical formulating for its binding and disintegrating properties, is sold in particular by BASF under the trade name Kollidon® VA 64.

In accordance with the invention, the weakly compressible diluting agent and the copolymer of 1-vinylpyrrolidin-2-one and of vinyl acetate are present in the pharmaceutical dosage form in a ratio by weight advantageously of between 1.5 and 30. Preferably, this ratio is between 3 and 22.

According to yet another advantageous arrangement of the invention, the weakly compressible diluting agent and the copolymer of 1-vinylpyrrolidin-2-one and of vinyl acetate together represent between 25 and 65% by weight of the total weight of the pharmaceutical dosage form.

As mentioned above, the presence of the copolymer of 1-vinylpyrrolidin-2-one and of vinyl acetate in the mixture of excipients makes it possible to confer, on the latter, a compressibility which is sufficiently high to produce a pharmaceutical dosage form of satisfactory hardness. However, in some cases and in particular when the pharmaceutical dosage form is intended to include an amount of active principle representing more than 25% by weight of the total weight of the pharmaceutical dosage form, it is possible to allow for the mixture of excipients to furthermore comprise a polyol capable of further increasing its compressibility.

According to the invention, this polyol is advantageously chosen from glucitols and diglucitols, such as mannitol, sorbitol, xylitol and lactitol, and represents at most 15% by weight of the total weight of the pharmaceutical dosage form.

The polyol is preferably granulated mannitol (such as that sold by Roquette under the trade name Pearlitol®), for a water-sensitive active principle (mannitol is not very hygroscopic), or granulated sorbitol (such as that sold by Roquette under the trade name Neosorb®), which also has a high compressibility.

The pharmaceutical dosage form in accordance with the invention can also comprise other excipients and in particular excipients chosen from fillers, flow agents, lubricating agents, flavor enhancers, sweetening agents and flavorings.

Thus, the pharmaceutical dosage form in accordance with the invention can comprise:

one or more fillers preferably chosen from microcrystalline cellulose, pregelatinized starch and carboxymethylcellulose; these fillers, the role of which is to accelerate the breakup of the pharmaceutical dosage form in the mouth without detrimentally affecting the hardness thereof, are advantageously present in proportions of between 10 and 30% by weight of the total weight of the pharmaceutical dosage form;

one or more flow agents preferably chosen from anhydrous colloidal silica, talc and stearic acid; these flow agents, which are intended, first, to prevent the components of the pharmaceutical dosage form from forming agglomerates during its preparation and, secondly, to reduce the effects of friction during the tableting, are advantageously present in proportions of between 0.1 and 0.5% by weight of the total weight of said pharmaceutical dosage form;

one or more lubricating agents preferably chosen from magnesium stearate, calcium stearate, stearic acid and glycerol dibehenate (Compritol®, Gattefosse); these lubricating agents, which are also intended to reduce the effects of friction during the tableting, are advantageously present in proportions of between 0.5 and 5% by weight of the total weight of the pharmaceutical dosage form;

one or more flavor enhancers, such as citric acid or sodium citrate; these flavor enhancers are advantageously present in proportions advantageously of between 0.5 and 5% by weight of the total weight of the pharmaceutical dosage form;

one or more sweetening agents, such as aspartame, saccharin sodium, potassium cyclamate or potassium acesulfame, and/or one or more flavorings, such as mint, raspberry, licorice, orange, lemon or strawberry; these sweetening agents and these flavorings, the role of which is to potentiate the effects of the flavor enhancer or enhancers and consequently to confer, on the pharmaceutical dosage form, a suitable taste, advantageously represent between 0.5 and 5% by weight of the total weight of the pharmaceutical dosage form.

The pharmaceutical dosage form in accordance with the invention can be used for the oral administration of a great many active principles. Mention may be made, as examples and without implied limitation, of analgesics, such as aspirin, paracetamol, ibuprofen, tramadol, codeine, dextropropoxyfene, buprenorphine, benorilate and morphine; antispasmodics, such as phloroglucinol; agents used in gastroenterology, such as cisapride, domperidone and metopimazine; agents for combating motion sickness, such as dimenhydrinate; antimigraines, such as dihydroergotamine and sumatripan; β-blockers, such as celiprolol and bisopropol; antihistaminics, such as loratadine, cetirizine and ketotifen; antibiotics or antibacterials of the β-lactamine, macrolide, quinolone or cephalosporin type; antivertigos, such as betahistine; and hypnotics, such as zopiclone, lorazepam, bromazepam, alprazolam and doxylamine, all these active principles being capable of being present alone or in combination.

In so far as the pharmaceutical dosage form in accordance with the invention exhibits an entirely suitable taste, whatever the taste of the active principle itself, this form is preferably an uncoated tablet. However, it is very clearly possible to envisage covering it with a fine film, for example of sugar, intended to render its contact with the buccal cavity, in particular with the tongue, even more pleasant.

Another subject matter of the present invention is a process for the preparation of a pharmaceutical dosage form in accordance with the invention, which process is characterized in that it comprises:

- mixing the active principle or principles with the weakly compressible diluting agent, the 1-vinylpyrrolidin-2-one copolymer and, if appropriate, the filler or fillers, flow agents, flavor enhancers, sweetening agents and flavorings,
- incorporating the lubricating agent or agents, if it is desired to use agents of this type, and
- tableting the resulting mixture.

This tableting can be carried out according to the same techniques and by means of the same equipment as those used for the preparation of conventional tablets and lozenges.

The pharmaceutical dosage form in accordance with the invention exhibits numerous advantages. This is because, in addition to exhibiting a disintegration in the mouth, a texture, a taste and a hardness which are highly satisfactory (the latter generally being between 70 and 150 N), it is characterized by the absence or the presence in a very small amount of a polyol, so that it significantly reduces the risks of side effects related to the ingestion of compounds of this type, in particular in the context of long-term treatment. Furthermore, it is capable of being obtained by a process which is simple to implement, in particular because it does not require any stage of coating of the active principle, and which is, for this reason, economically very attractive.

It is consequently capable of being used in a great many therapeutic indications, both in adults and in children. Its use is of very particular advantage in the treatment of symptoms or of pathologies requiring rapid relief. Mention may be made, as examples and without implied limitation, of headache, migraine, digestive spasms, vertigo, nausea, vomiting, allergic reactions, hypertension, coronary insufficiency and insomnia.

In addition to the preceding arrangements, the invention also comprises other arrangements which will emerge from the remainder of the description which follows and which relates to implementational examples of pharmaceutical dosage forms in accordance with the invention.

However, it should be clearly understood that these examples are given by way of illustration of the subject matter of the invention and do not constitute in any way a limitation thereof.

EXAMPLE 1

Preparation of Uncoated Tablets Comprising 500 mg of Paracetamol

Tablets each exhibiting the following qualitative and quantitative composition:

| | |
|---|---|
| Crystalline paracetamol | 500.0 mg |
| D-Glucose monohydrate | 597.6 mg |
| Copovidone | 35.2 mg |
| Microcrystalline cellulose | 160.0 mg |
| Anhydrous citric acid | 35.2 mg |
| Granulated sorbitol | 160.0 mg |
| Aspartame | 28.8 mg |
| Saccharin sodium | 14.4 mg |
| Glycerol dibehenate | 16.0 mg |
| Magnesium stearate | 6.4 mg |
| Orange flavoring | 46.4 mg | are prepared in the following way:

- all the components, with the exception of the lubricating agents (magnesium stearate and glycerol dibehenate), are mixed by means of a tumbler until a homogeneous whole is obtained,
- the magnesium stearate and the glycerol dibehenate are added and mixing is again carried out until homogeneous, then
- the resulting mixture is subjected to tableting in order to obtain tablets exhibiting a unit weight of 1.6 g which measure 20 mm in diameter and 4.5 mm in thickness.

The tablets thus prepared disintegrate in the mouth in 30 to 45 seconds.

EXAMPLE 2

Preparation of Uncoated Tablets Comprising 50 mg of Tramadol Hydrochloride

Tablets each exhibiting the following alitative and quantitative composition:

| | |
|---|---|
| Tramadol hydrochloride | 50.0 mg |
| D-Glucose monohydrate | 225.0 mg |
| Copovidone | 11.0 mg |
| Microcrystalline cellulose | 175.0 mg |
| Anhydrous citric acid | 11.0 mg |
| Aspartame | 7.5 mg |
| Saccharin sodium | 3.5 mg |
| Glycerol dibehenate | 5.0 mg |
| Stearic acid | 2.0 mg |
| Raspberry flavoring | 10.0 mg | are prepared by following a procedure similar to that described in Example 1, apart from the fact that the tableting is carried out so as to obtain tablets exhibiting a unit weight of 500 mg which measure 12 mm in diameter and 4 mm in thickness.

The tablets thus prepared disintegrate in the mouth in 30 to 40 seconds.

EXAMPLE 3

Preparation of Uncoated Tablets Comprising 200 mg of Ibuprofen

Tablets each exhibiting the following qualitative and quantitative composition:

| | |
|---|---|
| Ibuprofen | 200.0 mg |
| D-Glucose monohydrate | 378.0 mg |
| Copovidone | 80.0 mg |
| Microcrystalline cellulose | 180.0 mg |
| Anhydrous citric acid | 20.0 mg |
| Granulated mannitol | 80.0 mg |
| Aspartame | 20.0 mg |
| Saccharin sodium | 10.0 mg |

-continued

| | |
|---|---|
| Anhydrous colloidal silica | 2.0 mg |
| Magnesium stearate | 10.0 mg |
| Mint flavoring | 20.0 mg | are prepared by following a procedure similar to that described in Example 1, apart from the fact that the tableting is carried out so as to obtain tablets exhibiting a unit weight of 1 g which measure 16 mm in diameter and 5 mm in thickness.

The tablets thus prepared disintegrate in the mouth in 30 to 50 seconds.

EXAMPLE 4

Preparation of Uncoated Tablets Comprising 500 mg of Paracetamol

Tablets each exhibiting the following qualitative and quantitative composition:

| | |
|---|---|
| Paracetamol | 500.0 mg |
| Sucrose | 529.8 mg |
| Copovidone | 42.0 mg |
| Microcrystalline cellulose | 270.0 mg |
| Anhydrous citric acid | 33.0 mg |
| Aspartame | 52.5 mg |
| Anhydrous colloidal silica | 2.25 mg |
| Magnesium stearate | 15.0 mg |
| Orange flavoring | 3.5 mg | are prepared by following a procedure similar to that described in Example 1, apart from the fact that the tableting is carried out so as to obtain tablets exhibiting a unit weight of 1.5 g which measure 20 mm in diameter and 3.8 mm in thickness.

The tablets thus prepared disintegrate in the mouth in approximately 40 seconds.

What is claimed is:

1. Pharmaceutical dosage form uncoated tablet with the property of disintegration in the mouth in up to about 50 seconds comprising at least one active principal dispersed in a mixture of excipients, characterized in that the mixture of excipients comprises at least one weakly compressible diluting agent other than trehalos and a binding and disintegrating agent which is a copolymer of 1-vinyl pyrrolidin-2-one and of vinyl acetate, said weakly compressible diluting agent being present in a ratio by weight, with respect to said copolymer, of between 1.5 and 30 to 1.

2. Pharmaceutical dosage form according to claim 1, characterized in that the weakly compressible diluting agent is chosen from monosaccharides, disaccharides and dextrates.

3. Pharmaceutical dosage form according to claim 1, characterized in that the weakly compressible diluting agent is D-glucose monohydrate.

4. Pharmaceutical dosage form according to claim 1, characterized in that the copolymer of 1-vinylpyrrolidon-2-one; and of vinyl acetate is copovidone.

5. Pharmaceutical dosage form according to claim 1, characterized in that the weakly compressible diluting agent and the copolymer of 1-vinylpyrrolidin-2-one and of vinyl acetate are present in a ratio by weight of between 3 and 22.

6. Pharmaceutical dosage form according to claim 1, characterized in that the weakly compressible diluting agent and the copolymer of 1-vinylpyrrolidin-2-one and of vinyl acetate together represent between 25 and 65% by weight of the total weight of the pharmaceutical dosage form.

7. Pharmaceutical dosage form according to claim 1, characterized in that it comprises a polyol.

8. Pharmaceutical dosage form according to claim 7, characterized in that the polyol is chosen from glucitols and diglucitols and represents at most 15% by weight of the total weight of said pharmaceutical dosage form.

9. Pharmaceutical dosage form according to claim 8, characterized in that the polyol is granulated mannitol or granulated sorbitol.

10. Pharmaceutical dosage form according to claim 1, characterized in that the mixture of excipients comprises one or more fillers, flow agents, lubricating agents, flavor enhancers, sweetening agents and one or more flavorings.

11. Pharmaceutical dosage Bonn according to claim 10, characterized in that the fillers) is(are) chosen from microcrystalline cellulose, pregelatinized starch and carboxymethylcellulose and is(are) present in proportions of between 10 and 30% by weight of the total weight of said pharmaceutical dosage form.

12. Pharmaceutical dosage form according to claim 10, characterized in that the flow agent(s) is(are) chosen from anhydrous colloidal silica, talc and stearic acid and is(are) present in proportions of between 0.1 and 0.5% by weight of the total weight of said pharmaceutical dosage form.

13. Pharmaceutical dosage form according to claim 10, characterized in that the lubricating agent(s) is(are) chosen from magnesium stearate, calcium stearate, stearic acid and glycerol dibehenate and is(are) present in proportions of between 0.5 anal 2.5% by weight of the total weight of said, pharmaceutical dosage form.

14. Pharmaceutical dosage form according to claim 10, characterized in that the flavor enhancer(s) is(are) chosen from citric acid and sodium citrate and is(are) present in proportions advantageously of between 0.5 and 5% by weight of the total weight of said pharmaceutical dosage form.

15. Pharmaceutical dosage form according to claim 10, characterized in that the sweetening agent(s) and the flavoring(s) advantageously represent between 0.5 and 5% by weight of the total weight of said pharmaceutical dosage form.

16. Pharmaceutical dosage form according to claim 1, characterized in that the active principle is chosen analgesics, antispasmodics, agents used in gastroenterology, agents for combating motion sickness, antimigraines, β-blockers, antihistaminics, antibiotics or antibacterials, antivertigos and hypnotics, alone or in combination.

17. Pharmaceutical dosage form according to claim 1, characterized in that the active principle is paracetamol or tramadol.

18. Pharmaceutical dosage form according to claim 1, characterized in that it is an uncoated tablet.

19. Process for the preparation of a pharmaceutical dosage form according to claim 1, characterized in that it comprises:
  mixing the active principle or principles with the weakly compressible diluting agent, the 1-vinylpyrrolidin-2-one copolymer and, if appropriate, the filler or fillers, flow agents, flavor enhancers, sweetening agents and flavorings,
  incorporating the lubricating agent or agents, if it is desired to use agents of this type, and
  tableting the resulting mixture.

20. A pharmaceutical dosage form composition as claimed in claim 1 adapted, to be formed into a tablet.

21. A pharmaceutical dosage form composition as claimed in claim 1 in the form of a tablet.

* * * * *